United States Patent
Tokosh et al.

[11] Patent Number: 6,133,225
[45] Date of Patent: *Oct. 17, 2000

[54] SOAP BAR HAVING A RESISTANCE TO CRACKING AND THE METHOD OF MAKING THE SAME

[75] Inventors: Richard Tokosh, Saddle Brook; Andrew J. Cunningham, Park Ridge, both of N.J.

[73] Assignee: Avon Products, Inc., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/966,251

[22] Filed: Nov. 7, 1997

Related U.S. Application Data

[60] Provisional application No. 60/037,262, Jan. 31, 1997.

[51] Int. Cl.[7] .............................. C11D 13/00; A61K 7/50
[52] U.S. Cl. ........................... 510/458; 510/152; 510/153
[58] Field of Search ..................................... 510/151, 152, 510/153, 154, 155, 130, 458

[56] References Cited

U.S. PATENT DOCUMENTS

| | | | |
|---|---|---|---|
| 3,070,547 | 12/1962 | Chaffe | 252/121 |
| 4,147,053 | 4/1979 | Marchesani | 73/104 |
| 4,201,528 | 5/1980 | Fischer | 425/209 |
| 4,265,778 | 5/1981 | Sonenstein | 252/117 |
| 4,767,560 | 8/1988 | Gervasio | 252/108 |
| 4,861,507 | 8/1989 | Gervasio | 252/108 |
| 5,017,302 | 5/1991 | Colwell et al. | 252/134 |
| 5,154,849 | 10/1992 | Visscher et al. | 252/174.25 |
| 5,219,487 | 6/1993 | Heile, Jr. et al. | 252/108 |
| 5,417,876 | 5/1995 | Tokosh et al. | 252/108 |
| 5,602,088 | 2/1997 | Tokosh et al. | 510/144 |

*Primary Examiner*—Necholus Ogden
*Attorney, Agent, or Firm*—Ohlandt, Greeley, Ruggiero & Perle, LLP

[57] ABSTRACT

There is provided a bar soap having an improved resistance to cracking after exposure to repeated cycles of moistening and drying. The bar soap, which contain greater than 3 wt % glycerin, is prepared from an initial blend of about 60 wt % to about 85 wt % tallow, about 10 wt % to about 40 wt % coconut oil and about 15 wt % to about 35 wt % fatty acid. The present invention also relates to the process of transforming the initial blend into a bar soap having an improved resistance to wet cracking.

7 Claims, No Drawings

SOAP BAR HAVING A RESISTANCE TO CRACKING AND THE METHOD OF MAKING THE SAME

RELATED APPLICATION

The priority of U.S. Provisional Application Ser. No. 60/037,262, filed Jan. 31, 1997, is claimed.

BACKGROUND OF THE INVENTION

1. Field of Invention

Toilet soap bars based upon soap (alkali metal salts of fatty acids) are commonly used for cleansing the human body. While function is important, consumers are also concerned with the appearance of a soap product over its life.

There is a well-known tendency for a bar soap to form cracks after repeated cycles of exposure to moisture and subsequent drying. This tendency is called "wet cracking" (hereinafter "wet cracking" or "cracking") This is in undesirable characteristic as it causes the bar soap to assume an unpleasant appearance that consumers find displeasing.

Wet cracking is a result of several factors. Such factors include product shape, extrusion temperature, sodium chloride content, iodine value on the feed stock, inappropriate mixing during the extrusion process and coconut oil fatty acid content. However, one primary factor that contributes to wet cracking is a high glycerin content. Glycerin is also known in the art as glycerine or glycerol.

It is known that increased cranking will occur as a result of high coconut oil fatty acid (hereinafter "CNOFA") content. The addition of sodium cocoyl isethionate (hereinafter "SCI") will normally increase resistance to cracking in such a soap. However, when a soap bar contains greater than 3 weight percent glycerin, not only does the amount of wet cracking exhibited by the soap bar over its lifetime increase, but the effect of SCI to resist cracking exhibited is virtually loss. Until now, there has not been an effective reduction of wet cracking in a soap bar that contains greater than 3 weight percent glycerin.

2. Description of the Prior Art

Previous attempts have been made to reduce wet cracking. For example, U.S. Pat. No. 5,017.302 to Colwell et al describes the addition of a saturated long chain primary alcohol to reduce cracking.

U.S. Pat. No. 4,265,778 to Sonenstein describes the addition of about 0.1% to 15% of an anionic polymaleic electrolyte will reduce cracking.

U.S. Pat. No. 4,201,528 to Fischer describes a way to reduce cracking in a laminated bar by extruding the soap mass through aligned slots thus eliminating the spiral movement of the soap mass.

SUMMARY OF THE INVENTION

It is an object of the present invention to provide a soap bar that demonstrates little or no cracking when subjected to repeated cycles of wetting and drying.

It is also an object of the present invention to provide a soap bar that contains greater than 3 weight percent of glycerin, yet has a high resistance to cracking.

It is another object of the present invention to provide such a soap bar that has a pleasant color in addition to exhibiting a substantial decrease in wet cracking during the lifetime of the soap bar.

It is a further object of the present invention to provide such a soap bar that has a pleasant fragrance in combination with a substantial decrease in wet cracking during the lifetime of the soap bar.

It is yet another object of the present invention to provide a method of manufacturing a soap bar that demonstrates little or no cracking when subjected to repeated cycles of wetting and drying.

The present invention relates to a soap bar manufactured from an initial blend comprised of about 60 wt % to about 85 wt % tallow, about 10 wt % to about 40 wt % coconut oil and about 15 wt % to about 35 wt % fatty acid. The resultant soap bar comprises about 55 wt % to 70 wt % sodium tallowate, 5 wt % to 15 wt % sodium cocoate, 1 wt % to 3 wt % unreacted triglycerides, and 5 wt % to 10 wt % glycerin. Preferably, the glycerin is 6 wt % to 9 wt %. Preferably, the soap bar also includes about 0.2 wt % to about 8 wt % coconut oil fatty acid. More preferably, the soap bar includes about 4 wt % to about 7 wt % coconut oil fatty acid. Although the soap bar has about 5 wt % to about 10 wt % glycerin, the resultant soap bar has an unexpectedly high resistance to cracking. All percentages set forth herein are percentages by weight of the total composition. In its final composition, the soap bar, in addition to the above glycerin content, has a moisture content about 8 wt % to about 15 wt %.

The present invention also relates to the process of preparing a soap bar with a high resistance to cracking.

DETAILED DESCRIPTION OF THE PREFERRED EMBODIMENTS

A soap bar having a mixture of tallow and coconut oil is known. However, such a soap bar has readily produced cracking.

As stated above, the addition of SCI will increase resistance to cracking in the resultant soap that occurs as a result of CNOFA. However, when the soap bar contains greater than 3 weight percent of glycerin, the addition of SCI does not have a marked effect on reducing cracking.

The present invention discovered that a soap bar produced from a preferred blend of about 60 wt % to about 85 wt % tallow, about 10 wt % to about 40 wt % coconut oil, and about 15 wt % to about 35 wt % fatty acid, unexpectedly exhibited a consistent resistance to cracking, yet the glycerin content is over 3 weight percent. In the preferred embodiment, the about 25 wt % fatty acid is derived from about 85 wt % tallow and about 15 wt % coconut oil. Although applicants do not wash to be bound by any theory, it is believed that the unreacted triglycerides and the glycerin produce a synergism that reduces the extent of cracking exhibited by the resultant soap bar.

Prior art soaps formed from tallow oil and coconut oil produce too much glycerin for processing in soap making equipment specifically designed for manufacturing soap from fatty acids, such as a Mazzoni "SC" plant. The addition of fatty acids to the tallow/coconut oil blend reduces the level of glycerin byproduct. Thus, the decrease in resultant glycerin content allows the present invention to be manufactured in equipment previously believed to be unable to accommodate a tallow/coconut oil/fatty acid blend.

Also, the synergistic effect of the blend of the tallow, coconut oil, and fatty acids results in a soap bar that exhibits a resistance to cracking despite having a relatively high amount of glycerin. In addition, the present invention represents an improvement over prior attempts to remedy the issue of wet cracking since no new equipment is necessary to achieve this improved soap.

In a preferred embodiment, the soap bar also has about 3 wt % to about 8 wt % coconut oil fatty acid to improve the lather characteristics of the finished soap bar. In its most preferred embodiment, the soap bar has about 63 wt % sodium tallowate, about 11 wt % sodium cocoate, about 1 wt % to about 3 wt % unreacted triglycerides, and about 6 wt % to 3 wt % glycerin that is derived from tallow and coconut oil. The resultant soap will greatly reduce or eliminate wet cracking.

Coconut oil fatty acid may be added to neutralize any free alkalinity of the processed soap base. However, the addition of coconut oil fatty acid is not required for the effectiveness of the present invention. In addition, other fatty acids may be used. Examples of fatty acids that may be used are those fatty acids derived from tallow, palm oil and babassu oil.

The first step in the process of preparing a soap bar of the present invention is the selection of the base. A composition of 63.75 wt % tallow, 11.25 wt % coconut oil and 25 wt % fatty acid is the most preferred initial blend. They react to provide a "neat soap," a term well known in the art. However, other combinations of ingredients within the ranges set forth above and that are appropriate for soap bar manufacturing, may be used.

In the preferred embodiment, a Mazzoni SC plant is used. Sufficient heat is applied to the aforementioned tallow/coconut oil/fatty acid blend so that the blend is preheated to a temperature range of preferably from about 140° F. to about 160° F. Preheating to a temperature within this range is advised in order to achieve a practical reaction rate when the blend is reacted with sodium hydroxide (hereinafter "NaOH") in the next step to produce neat soap. Although the amount of sodium hydroxide required may vary according to the acid value of the tallow/coconut oil/fatty acid blend, preferably about 18.2 wt % of a 50 wt % solution of sodium hydroxide is added to 62.4 wt % of the tallow/coconut oil/fatty mixture.

The reacted product of neat soap contains about 5 wt % to about 10 wt % glycerin, about 1 wt % to about 3 wt % unreacted triglycerides, and about 30 wt % to about 35 wt % moisture.

When these ingredients are homogenous within the soap mass, the content of excess sodium hydroxide, which is present at about 0.01 wt % to about 0.1 wt %, may be reduced by any means presently known in the art. This step is not required. In a preferred embodiment, about 2 wt % to about 8 wt % CNOFA is injected into the soap mass to reduce any excess NaOH. In a more preferred embodiment, about 5 wt % CNOFA is injected into the soap mass to eliminate any excess NaOH. As stated above, although coconut oil fatty acids are known in the art to improve lather characteristics of the finished product, other fatty acids may be used.

The soap mass must then be dried to decrease the moisture content to about 8 wt % to about 15 wt %. In the preferred embodiment, a Mazzoni soap dryer is used to decrease the moisture content. However, other soap dryers known in the art may be used.

After drying, the soap mass is preferably agitated. In one embodiment, the soap mass is placed into an amalgamator having an agitator, and the agitator is initiated. At this time, a fragrance or fragrances may be added. Preferably, the fragrance is added in an amount about 0.1 wt % to about 3 wt %. The composite is allowed to mix for approximately two minutes. At this point, any colorants may be added to the mixture. The soap composite with or without fragrance and/or colorant is preferably allowed to mix for approximately an additional three minutes. The total preferred mixing time is approximately five minutes.

After mixing, the composite is extruded. The extrusion step can be performed through any device available in the soap making industry to generate a homogenous mass. A preferred device is a 300 mm Mazzoni "simplex" plodder. In one preferred embodiment, two 300 mm Mazzoni "simplex" plodders and one Mazzoni duplex plodder are used. In the preferred embodiment, the first simplex plodder is preferably fitted with a 0.5 mm screen and the second simplex plodder is fitted with a 0.3 mm screen. The duplex plodder has a 0.3 mm screen in its vacuum chamber. The screen size utilized will vary from about 0.1 mm to about 3.0 mm depending on the consistency of the soap mass being extruded.

After a homogenous mass is created, the composite is transferred to a vacuum extruder to extrude the homogenous composite into billets. In the preferred embodiment, a 300 mm Mazzoni duplex vacuum extruder is used. In the preferred embodiment, the 300 mm Mazzoni duplex vacuum extruder is equipped with a 0.3 mm screen and the vacuum LS set to about 25 inches Hg to about 27 inches Hg. In the most preferred embodiment, the vacuum is set to about 26 inches Hg.

After extrusion into billets, the billets are cut into desired length, preferably on a Mazzoni automatic cutter, and then pressed into the desired shape.

EXAMPLES

Because it is known by experts in the industry that data generated on laboratory or pilot plant equipment may not be reproducible on a plant scale, all samples were prepared on commercial equipment.

All samples were subjected to exaggerated laboratory testing of wet and drying cycles to simulate consumer use. Specifically, twelve (12) samples were totally immersed in 77° F. water for one hour and allowed to air dry at ambient temperature for twenty-three hours. The bars were then snored on a scale of 0 to 6, with zero (0) representing no cracks and six (6) being the most severe degree of cracking. In order to be consistent during the scoring, all samples were compared against a photographic display that represented the degree of cracking for a particular score. The photographic display scores were as follows: Zero (0)=no cracks; One (1)=very slight cracks; Two (2)=slight cracks; Three (3)=slight to moderate cracks; Four (4)=moderate cracks; Five (5)=moderate to excessive cracks; Six (6)=excessive cracks. After scoring, the samples were again immersed in 77° F. water for one hour and allowed to air dry at ambient temperature for twenty-three hours. Thereafter, the samples were then again scored. The samples were subjected to a total of three such immersion/drying cycles.

Example 1

A soap base was prepared by reacting a blend of 85 wt % tallow fatty acid/15 wt % coconut oil fatty acid with sodium hydroxide. After completion of the reaction, approximately 5 wt % coconut oil fatty acid and 2 wt % glycerin was injected into the neat soap before drying the soap mass to 8 wt % to 15 wt % moisture.

After drying, fragrance and colorants were added to the soap mass prior to processing into bars. Additionally, SCI was added to SAMPLE A. The resultant soap bars were then evaluated for cracking according to the method described above.

| INGREDIENTS | Weight-Percent |
|---|---|
| CONTROL | |
| Soap base | 96.7996 |
| Fragrance | 2.5000 |
| Titanium Dioxide | 0.7000 |
| Iron Oxide Black | 0.0004 |
| SAMPLE A | |
| Soap base | 93.5496 |
| Fragrance | 2.5000 |
| Titanium Dioxide | 0.7000 |
| Iron Oxide Black | 0.0004 |
| Sodium Cocoyl Isethionate (SCI) | 3.2500 |

WET CRACKING RESULTS

| | THIRD CYCLE | ACCEPTABLE | | | | UN-ACCEPTABLE | | |
|---|---|---|---|---|---|---|---|---|
| | AVERAGE | 0 | 1 | 2 | 3 | 4 | 5 | 6 |
| CONTROL | 3.8 | 0 | 0 | 0 | 2 | 10 | 0 | 0 |
| SAMPLE A | 1.5 | 0 | 6 | 6 | 0 | 0 | 0 | 0 |

These results show that a product with the standard superfatted base will result in unacceptable wet cracking. However, the results also show that the incorporation of sodium cocoyl isethionate into the soap formula will reduce wet cracking characteristics as illustrated by SAMPLE A.

Example 2

A soap base was prepared by reacting a blend of 85 wt % tallow fatty acid/15 wt % coconut oil fatty acid with sodium hydroxide. After the reaction was complete, approximately 5 wt % glycerin and approximately 0.25 wt % CNOFA were injected into the neat soap before the neat soap was fried to 8 wt % to 15 wt % moisture.

After the neat soap was dried the following formulations were prepared, processed into bars and evaluated for wet cracking using the same method as in EXAMPLE 1.

| INGREDIENTS | Weight Percent |
|---|---|
| SAMPLE B | |
| Soap base | 96.9480 |
| Fragrance | 2.0000 |
| Titanium Dioxide | 1.0000 |
| Iron Oxide Yellow | 0.0400 |
| Cosmetic Brown | 0.0020 |
| Cosmetic Tan | 0.0100 |
| SAMPLE C | |
| Soap base | 93.6980 |
| Fragrance | 2.0000 |
| Titanium Dioxide | 1.0000 |
| Iron Oxide Yellow | 0.0400 |
| Cosmetic Brown | 0.0020 |
| Cosmetic Tan | 0.0100 |
| Sodium Cocoyl Isethionate (SCI) | 3.2500 |

WET CRACKING RESULTS

| | THIRD CYCLE | ACCEPTABLE | | | | UN-ACCEPTABLE | | |
|---|---|---|---|---|---|---|---|---|
| | AVERAGE | 0 | 1 | 2 | 3 | 4 | 5 | 6 |
| SAMPLE B | 3.2 | 0 | 0 | 2 | 6 | 4 | 0 | 0 |
| SAMPLE C | 3.6 | 0 | 0 | 0 | 5 | 7 | 0 | 0 |

These results show that a product that is formed from a soap base comprised of 100 wt % fatty acid and that has 5 wt % glycerin will result in borderline acceptability in wet cracking. Also evident from the results is that the addition of SCI into the formula did not have the positive effect on wet cracking that was evident with Sample A.

Example 3

For SAMPLE D, a soap base was prepared by the method set forth in Example 1. For SAMPLE E, a soap base was prepared according to the method of the present invention.

After the neat soap was dried the following formulations were prepared, processed into bars and evaluated for wet cracking using the same method as in EXAMPLE. 1.

| INGREDIENTS | % |
|---|---|
| SAMPLE D | |
| Soap base (with 5 wt % CNOFA, 2 wt % glycerin) | 92.1419 |
| Fragrance | 2.5000 |
| Titanium Dioxide | 2.0000 |
| Iron Oxide Yellow | 0.1010 |
| Ultramarine Blue | 0.0001 |
| FD&C Yellow #6 | 0.0070 |
| Sodium Cocoyl Isethionate | 3.2500 |
| SAMPLE E | |
| Soap base (with about 7 wt % glycerin, 5 wt % CNOFA, & about 1 wt % to about 3 wt % unreacted triglycerides) | 95.3919 |
| Fragrance | 2.5000 |
| Titanium Dioxide | 2.0000 |
| Iron Oxide Yellow | 0.1010 |
| Ultramarine Blue | 0.0001 |
| FD&C Yellow | 0.0070 |

WET CRACKING RESULTS

| | THIRD CYCLE | ACCEPTABLE | | | | UN-ACCEPTABLE | | |
|---|---|---|---|---|---|---|---|---|
| | AVERAGE | 0 | 1 | 2 | 3 | 4 | 5 | 6 |
| CONTROL | 4.8 | 0 | 0 | 0 | 0 | 2 | 10 | 0 |
| SAMPLE D | 1.5 | 0 | 6 | 6 | 0 | 0 | 0 | 0 |

Past experimentation, exemplified above, exhibited that while the addition of SCI may improve wet cracking, the improvement is inconsistent and appears to depend upon the contents of the soap bar. Compare SAMPLE A (average cracking value=1.5) with SAMPLE D (average cracking value=4.8). However, the production of soap from the base having a fatty acid blend of this invention, consistently yielded improved resistance to wet cracking.

The invention is not limited to the examples illustrated above, as it is understood that one ordinarily skilled in the art would be able to utilize substitutes and equivalents without departing from the invention.

What is claimed is:

1. A method of manufacturing a soap mass that can produce a soap bar that is resistant to cracking, the method comprising the steps of:

combining about 60 wt % to about 85 wt % tallow, about 10 wt % to about 40 wt % coconut oil, and about 15 wt % to about 35 wt % fatty acid to form a soap blend;

pre-heating said soap blend;

reacting said pre-heated soap blend with an amount of sodium hydroxide to produce an incompletely saponified neat soap having from about 1 wt % to about 3 wt % of unreacted triglycerides and from about 5 wt % to about 10 wt % glycerin; and drying said incompletely saponified neat soap to produce a soap mass comprising about 10 wt % to 15 wt % moisture.

2. The method of claim 1, further comprising the steps of:

amalgamating said soap mass with fragrance and/or colorant to form an amalgamated soap composition;

extruding said amalgamated soap composition to formed an extruded soap composition; and forming a soap bar from said extruded soap composition.

3. The method of claim 1, wherein said pre-heating of said blend is to a temperature from about 140° F. to about 160° F.

4. The method of claim 1, further comprising the step of:

reducing the amount of said sodium hydroxide in said neat soap injecting a sufficient amount of fatty acid to reduce alkalinity prior to drying said neat soap composition.

5. The method of claim 4, wherein the amount of said sodium hydroxide in said neat soap is eliminated by injecting a sufficient amount of fatty acid to reduce the alkalinity prior to drying said neat soap.

6. The method of claim 4, wherein the amount of said neat sodium hydroxide is reduced by injecting between about 3 wt % to 8 wt % coconut oil fatty acid into said soap composition.

7. The method of claim 5, wherein the amount of said sodium hydroxide is reduced by injecting about 5 wt % coconut oil fatty acid into said neat soap composition.

* * * * *

UNITED STATES PATENT AND TRADEMARK OFFICE
CERTIFICATE OF CORRECTION

PATENT NO. : 6,133,225

DATED : October 17, 2000

INVENTOR(S) :. Tokosh, Richard et al.

It is certified that error appears in the above-identified patent and that said Letters Patent is hereby corrected as shown below:

Column 10, line 9; after "soap" insert therefore --by--
Column 10, line 9; after "amount of" insert therefore --a--
Column 10, line 10; after "soap" delete therefore "composition"
Column 10, line 14; after "amount of" insert therefore --a--
Column 10, line 16; after "where in" detelete therefore "the amount of"
Column 10, line 16; after "said neat" insert therefore --soap--
Column 10, line 17; delete "sodium hydroxide"
Column 10, line 20; after "wherein" delete therefore "the amount of"
Column 10, line 21; delete "sodium hydroxide" and insert therefore --neat soap--
Column 10, line 22; after "said" delete therefore "neat"

Signed and Sealed this

Eighth Day of May, 2001

Attest:

NICHOLAS P. GODICI

Attesting Officer     Acting Director of the United States Patent and Trademark Office